United States Patent
Polkus et al.

(12)

(10) Patent No.: US 6,375,354 B1
(45) Date of Patent: Apr. 23, 2002

(54) METHOD AND SYSTEM FOR DETERMINING A VARIABLE LATERAL CENTER-TO-CENTER SETPOINT FOR A DIGITAL IMAGING SYSTEM

(75) Inventors: Vincent S. Polkus, Delafield; Jon C. Omernick, Wauwatosa; Mark A. Hammel, Waukesha, all of WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/576,512

(22) Filed: May 23, 2000

(51) Int. Cl.$^7$ .................................................. A61B 5/08
(52) U.S. Cl. ...................................................... 378/205
(58) Field of Search ................................ 378/205, 98.8

Primary Examiner—Craig E. Church
(74) Attorney, Agent, or Firm—Fletcher, Yoder & Van Someren (57) ABSTRACT

A method is provided for automatically determining a variable laterally centered setpoint for a digital radiographic imaging system that includes a radiation source and a digital detector. The variable laterally centered setpoint is determined during a setup procedure which involves providing a detector at a detector location, positioning the radiation source at a first source location, detecting a radiation field generated by the source while at the first source location, determining the lateral centerline of the detected radiation field, repositioning the source to a second source location that is laterally displaced from the first location, detecting a second radiation field, and determining the lateral centerline of the second radiation field. A lateral gain constant for the imaging system can then be determined based on the determined centerlines of the first and second radiation fields and feedback signals from position sensors that are representative of the first and second source locations. Based on the lateral gain constant and the source position feedback signal, the source can be laterally centered with respect to the lateral centerline of the detector.

30 Claims, 3 Drawing Sheets

POSITION "A"

METHOD AND SYSTEM FOR DETERMINING A VARIABLE LATERAL CENTER-TO-CENTER SETPOINT FOR A DIGITAL IMAGING SYSTEM

FIELD OF THE INVENTION

The present invention relates generally to digital imaging systems and, more particularly, to a system and setup procedure for determining a variable setpoint for laterally centering a radiation source with respect to a digital detector in a digital imaging system.

BACKGROUND OF THE INVENTION

The installation and setup procedure for digital imaging systems, such as digital radiographic imaging systems, can be complex and time-consuming. To comply with customer image quality and consistency requirements and various regulatory and safety standards, the procedure generally requires the determination of a variety of constants including the positioning of the x-ray source with respect to the detector. For example, the determination and establishment of fixed setpoints for laterally centering the x-ray source with respect to the center of the detector often is a required procedure. Among the problems associated with the failure to accurately determine lateral center-to-center setpoints in radiographic imaging system are image decentering and cutoff Generally, known installation and setup procedures for determining lateral center-to-center setpoints require that a field engineer geometrically determine the lateral centerline of the detector and then generate and detect several x-ray fields with the x-ray source located at a variety of positions laterally displaced from one another. Eventually, through trial and error, the field engineer can determine a laterally centered source position at which the x-ray field generated by the source is laterally centered with respect to the lateral centerline of the detector when the detector is fixed at a particular position. Once the laterally centered source position is found, the field engineer sets a fixed detent setpoint to mark the location. For example, the field engineer may install an electromechanical switch or other device in the ceiling or the superstructure of the x-ray source that will tactilely, and perhaps audibly, indicate to users of the imaging system that the x-ray source is at a laterally centered position.

This iterative setup procedure becomes even more complex when the detector is movable between locations. In such event, the field engineer must repeat the setup procedure at multiple locations of the detector and install several setpoint or detent devices at the corresponding multiple laterally centered source positions. Still further, many examination rooms may include more than one detector that can be used with the same x-ray source. For example, an examination room may include a horizontal patient table with a first detector that is movable along the longitudinal axis of the table, as well as an upright positioner with a second detector that is movable along the vertical axis of the positioner. Such a setup requires the determination of laterally centered source positions with respect to multiple detector positions for each detector.

Once a laterally centered source position is determined and marked with a setpoint device (e.g., a tactile switch), the position is fixed. Thus, a user of the imaging system is not afforded flexibility in the event that the user might desire to position the detector in a position other than the positions for which laterally centered setpoints were determined. Accordingly, even though a detector could be continuously movable along a track such that patients of various sizes could be accommodated or various anatomical parts could be more easily imaged, the positions in which the detector could accurately be used would be restricted to only those few detector positions which had corresponding fixed source setpoints. Otherwise, image decentering or cutoff may occur.

Fixed setpoints can also result in decreased system reliability because the physical switches or detent devices increase the number of components which can potentially fail during system usage.

Thus, it would be desirable to provide a system and method for setting up a digital radiographic imaging system that would avoid time-consuming iterative procedures for determining source positions setpoints that are laterally centered with respect to the lateral centerline of the detector. It would be further desirable if such a setup system and method would result in the elimination of fixed setpoints and physical fixed setpoint devices, thus affording greater flexibility and increasing the reliability of the system.

SUMMARY OF THE INVENTION

The present invention addresses one or more of the shortcomings noted above.

For example, a method for determining a lateral center-to-center setpoint for a digital imaging system having a digital detector and a radiation source includes positioning a detector having a lateral centerline at a first detector position, positioning the radiation source at a first source position, generating a first radiation field that is detectable by the detector, detecting the first radiation field at the detector, and determining a first lateral centerline of the first radiation field. The radiation source is then positioned at a second source position that is displaced from the first source position at least in a lateral direction, followed by generating a second radiation field that is detectable by the detector, detecting the second radiation field at the detector, and determining a second lateral centerline of the second radiation field. A lateral gain constant may then be determined based on the determined first and second lateral centerlines and the first and second source positions.

In another aspect of the present technique, a method for determining a lateral center-to-center setpoint of a digital imaging system having a radiation source that generates a radiation field detectable by a digital detector is provided. The method includes determining a first lateral centerline of a first detected radiation field generated when the radiation source is at a first source position, determining a second lateral centerline of a second detected radiation field generated when the radiation source is at a second source position laterally displaced from the first source position, and determining a system gain constant based on the determined first and second lateral centerlines and the first and second source positions. The system gain constant may then be utilized to automatically determine a laterally centered source position at which a radiation field generated by the source is substantially laterally centered with respect to a lateral centerline of the detector.

In another aspect of the technique, a system is provided for automatically determining a lateral center-to-center setpoint of a radiation source with respect to a digital detector. The system includes a radiation source to generate a radiation field, the radiation source being movable at least along a source lateral axis and configured to generate a first radiation field at a first source position and a second radiation field at a second source position laterally displaced from the first source position. The system further includes a digital detector having a lateral centerline, the digital detector being configured to detect the first and second radiation fields and to generate detector signals representative thereof. The system also includes a processing module that is configured to determine a first lateral centerline of the first radiation field based on the detector signals representative of the first radiation field, determine a second lateral centerline of the second radiation field based on the detector signals representative of the second radiation field, and determine a lateral gain constant based on the first and second lateral centerlines and the first and second source positions.

DETAILED DESCRIPTION OF THE INVENTION

The following detailed description is made with reference to a digital radiographic imaging system having an x-ray source and a digital detector configured to detect x-ray beams generated by the source. It should be understood, however, that the system and method described hereafter can be implemented in other types of digital imaging systems which have a source that generates radiation other than in the x-ray spectrum (e.g., visible light, infrared, etc.). In such imaging systems, an appropriate digital detector is provided which is configured to detect the particular type of radiation generated by the radiation source.

Figure 1:
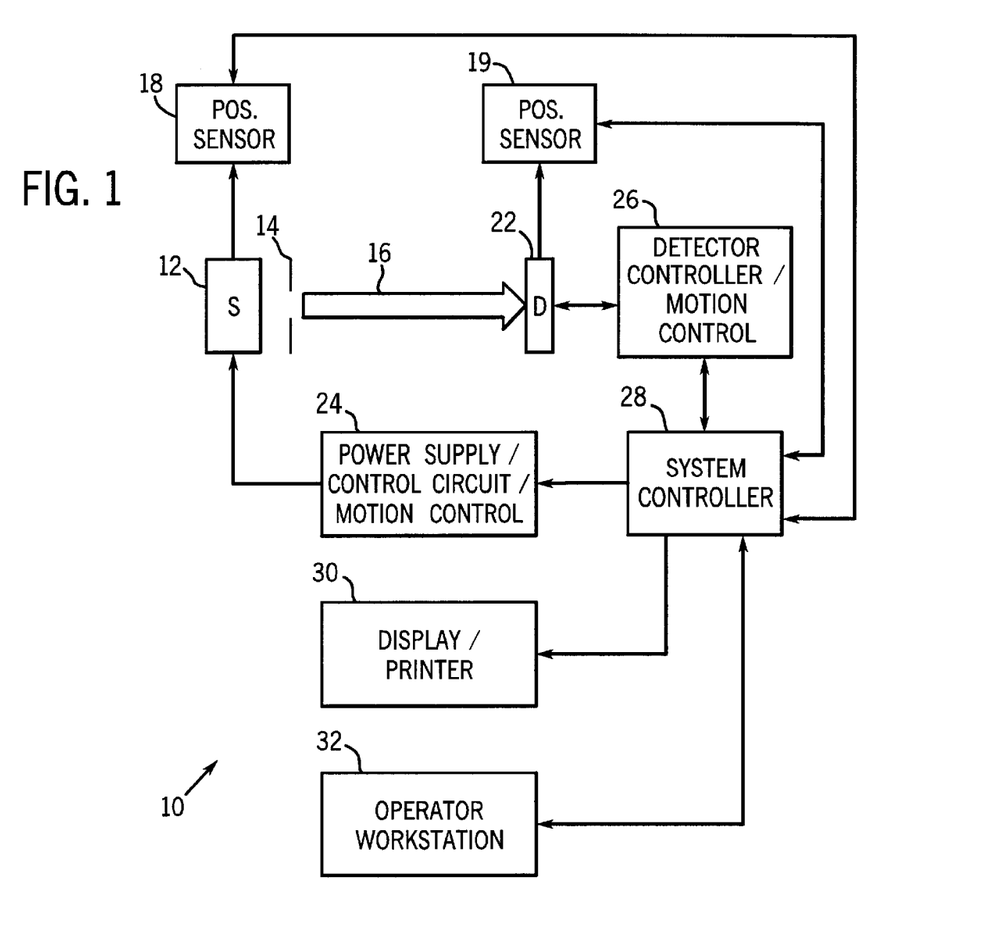
FIG. 1 is a diagrammatical overview of a digital x-ray imaging system in which the present technique is incorporated.

Turning now to the figures, FIG. 1 illustrates diagrammatically an imaging system 10 for acquiring and processing discrete pixel image data. In the illustrated embodiment, system 10 is a digital x-ray system that facilitates installation and setup procedures such that accurate image data can subsequently be acquired and processed by system 10 for output and display. In the embodiment illustrated in FIG. 1, imaging system 10 includes a source of x-ray radiation 12 configured to generate an x-ray field, referenced generally by the numeral 16, that impacts and is detected by a digital x-ray detector 22. Detector 22 converts the x-ray photons received on its surface to lower energy photons, and subsequently to electrical signals which are acquired and processed to reconstruct an image.

In an exemplary embodiment, system 10 is located in an examination room. The examination room may include, for example, a horizontal patient positioner or table for positioning a subject, such as a patient, to be imaged. The horizontal table or positioner may include a track disposed along a translational axis (e.g. the longitudinal axis) of the table for moving a detector 22 from one end of the table to another. Movement of detector 22 adds flexibility to system 10, because a movable detector allows various anatomical parts of a patient to be imaged without requiring repositioning of the patient and more easily accommodates patients of various sizes.

The examination room may also include an upright, or vertical, positioner against which a subject, such as a patient, may be positioned. Such an upright positioner may include a track disposed along a translational axis of the positioner such that a detector 22 may be moved between upper and lower vertical positions. Again, such movement advantageously allows accommodation of subjects of different sizes and/or facilitates imaging of different anatomical targets.

In an exemplary embodiment, the examination room includes an x-ray source 12 which is movable in longitudinal, lateral, and vertical directions (as well as about two angular degrees of freedom), such that the source can be positioned to generate an x-ray field that may be detected by a detector 22 associated with a horizontal patient positioner or a detector 22 associated with a vertical positioner. For example, the source 12 may be movable in the longitudinal direction along a track mounted to the ceiling of the examination room or the superstructure which supports the source 12. Such a track generally is positioned such that it is substantially parallel to the track of the horizontal patient positioner along which the detector 22 may be moved. The source 12 may also be movable laterally with respect to the longitudinal direction, as well as vertically with respect to the longitudinal direction. Further, the source may be arranged to angularly rotate such that the same source may be used in conjunction with either a detector 22 associated with a horizontal positioner or a detector 22 associated with an upright positioner.

In the embodiment illustrated in FIG. 1, imaging system 10 further includes a source position sensor 18 to provide an electrical signal representative of the position of the source 12 in the longitudinal, lateral, and/or vertical directions. System 10 further includes a detector position sensor 19 to detect the position of the detector 22 with respect to the translational axis of the horizontal positioner or of the upright positioner. Exemplary position sensors 18 and 19 are continuous position sensors, such as optical encoders, potentiometers, etc.

Source 12 is controlled by a power supply/control circuit 24 which provides both power and control signals for installation and setup procedures, as well as for examination sequences. In an exemplary embodiment, control circuit 24 may further include positioning or motion control elements, such as motor drive circuitry and a motor, to position the source 12 along any of the longitudinal, lateral, and vertical axes. As further illustrated in FIG. 1, detector 22 is coupled to a detector controller 26, which commands acquisition of the imaging signals generated in the detector. Detector controller 26 may also execute various signal processing and filtration functions, such as for initial adjustment of dynamic ranges, interleaving of digital image data, and so forth. Detector controller 26 may also include positioning or motion control elements, such as motor drive circuitry and a motor, for positioning the detector 22 along the translational axis of the patient positioner.

Both power supply/control circuit 24 and detector controller 26 are responsive to signals from a system controller 28. In general, system controller 28 commands operation of the imaging system to execute installation and set up procedures, including generation of command signals to control movement and positioning of source 12 and detector 22. System controller 28 also commands operation of the imaging system to execute examination protocols and to process acquired image data. In the present context, system controller 28 includes signal processing circuitry, typically based upon a general purpose or application-specific digital computer, associated memory circuitry for storing programs and routines executed by the computer, as well as configuration parameters and image data, interface circuits, and so forth. In the embodiment illustrated in FIG. 1, system controller 28 (or any suitable processing module), in accordance with a stored setup program, receives feedback signals from position sensors 18 and 19 and image data from detector controller 26, and processes the signals and data to determine a variable laterally centered setpoint position of source 12 with respect to the position of detector 22, as will be explained in detail below.

In the embodiment illustrated in FIG. 1, system controller 28 is also linked to at least one output device, such as a display or printer, as indicated at reference numeral 30. The output device may include standard or special purpose computer monitors and associated processing circuitry. One or more operator workstations 32 may be further lined in the system for outputting system parameters, controlling installation and setup procedures, requesting and controlling the setup of examinations, viewing images, and so forth. In general, displays, printers, workstations, and similar devices supplied within the system may be local to the data acquisition components, such as located physically within the examination room, or may be remote from these components, such as elsewhere within an institution or hospital, or in an entirely different location, linked to the image acquisition system via one or more configurable networks, such as the Internet, virtual private networks, and so forth.

Figure 2:
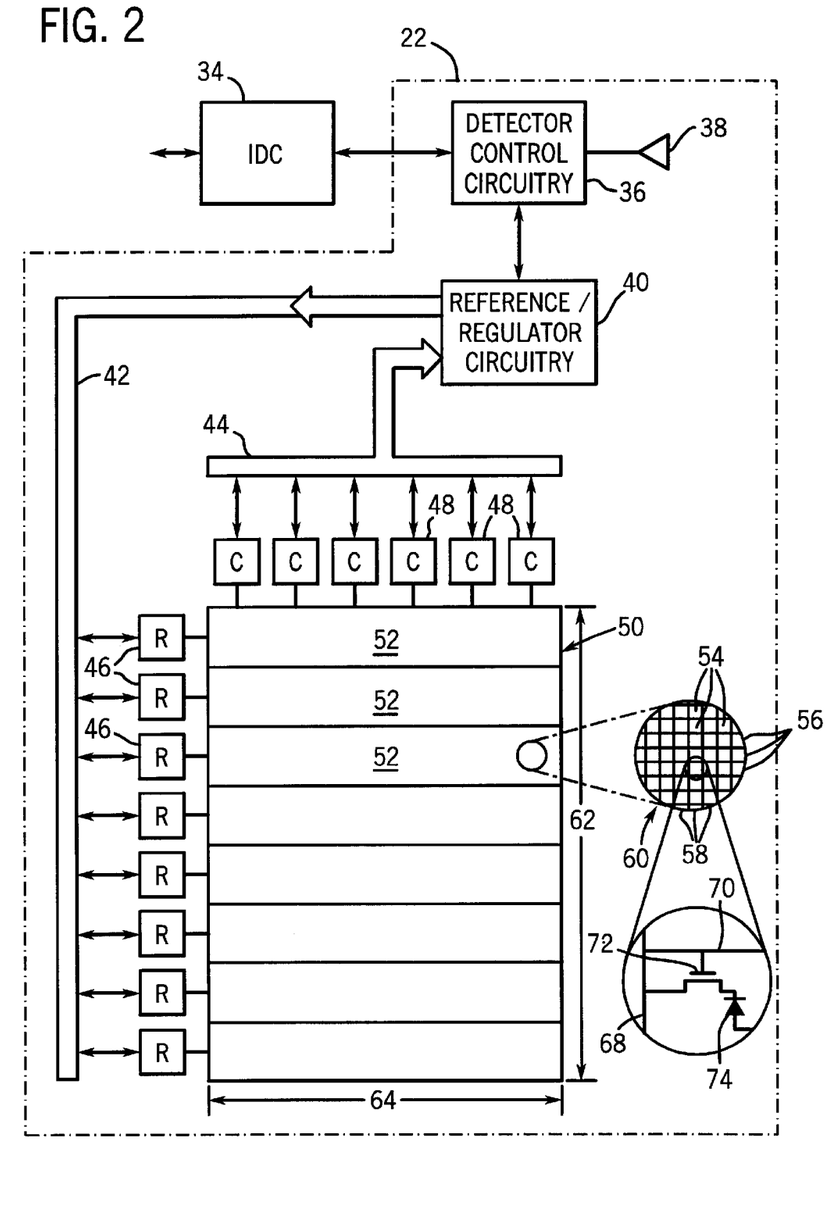
FIG. 2 is a diagrammatical representation of certain of the functional circuitry for producing image data in a detector of the system of FIG. 1.

FIG. 2 is a diagrammatical representation of functional components of an exemplary digital detector 22. FIG. 2 also represents an imaging detector controller or IDC 34 which will typically be configured within detector controller 26. IDC 34 includes a CPU or digital signal processor, as well as memory circuits for commanding acquisition of sensed signals from the detector. IDC 34 is coupled via two-way fiberoptic conductors to detector control circuitry 36 within detector 22. IDC 34 thereby exchanges command signals for image data within the detector during operation.

Detector control circuitry 36 receives DC power from a power source, represented generally at reference numeral 38. Detector control circuitry 36 is configured to originate timing and control commands for row and column drivers used to transmit signals during data acquisition phases of operation of the system. Circuitry 36 therefore transmits power and control signals to reference/regulator circuitry 40 and receives digital image pixel data from circuitry 40.

In the exemplary embodiment illustrated, detector 22 includes a scintillator that converts x-ray photons received on the detector surface during examinations to lower energy (light) photons. An array of photodetectors then converts the light photons to electrical signals which are representative of the number of photons or the intensity of radiation impacting individual pixel regions of the detector surface. Readout electronics convert the resulting analog signals to digital values that can be processed, stored, and displayed, such as in a display 30 or a workstation 32, following reconstruction of the image. In a present form, the array of photodetectors is formed on a single base of amorphous silicon. The array elements are organized in rows and columns, with each element consisting of a photodiode and a thin film transistor. The cathode of each diode is connected to the source of the transistor, and the anodes of all diodes are connected to a negative bias voltage. The gates of the transistors in each row are connected together and the row electrodes are connected to the scanning electronics. The drains of the transistors in a column are connected together and an electrode of each column is connected to readout electronics.

In the embodiment illustrated in FIG. 2, by way of example, a row bus 42 includes a plurality of conductors for enabling readout from various columns of the detector, as well as for disabling rows and applying a charge compensation voltage to selected rows, where desired. A column bus 44 includes additional conductors for commanding readout from the columns while the rows are sequentially enabled. Row bus 42 is coupled to a series of row drivers 46, each of which commands enabling of a series of rows in the detector. Similarly, readout electronics 48 are coupled to column bus 44 for commanding readout of all columns of the detector.

In the illustrated embodiment, row drivers 46 and readout electronics 48 are coupled to a detector panel 50 which may be subdivided into a plurality of sections 52. Each section 52 is coupled to one of the row drivers 46 and includes a number of rows. Similarly, each column driver 48 is coupled to a series of columns. The photodiode and thin film transistor arrangement mentioned above thereby define a series of pixels or discrete picture elements 54 which are arranged in rows 56 and columns 58. The rows and columns define an image matrix 60, having a known height 62 and a known width 64.

As also illustrated in FIG. 2, each pixel 54 is generally defined at a row and column crossing, at which a column electrode 68 crosses a row electrode 70. As mentioned above, a thin film transistor 72 is provided at each crossing location for each pixel, as is a photodiode 74. As each row is enabled by row drivers 46, signals from each photodiode may be accessed via readout electronics 48, and converted to digital signals for subsequent processing and image reconstruction.

Before imaging system 10 may be used to perform examination sequences, system 10 is properly installed and set up to ensure compliance with customer needs, performance requirements, and various regulatory standards. A performance variable used in this process is the center-to-center accuracy of the system 10. The center-to-center accuracy refers to the distance between the geometric center of the detector and the geometric center of the x-ray field as measure in the plane of the detector. One component of the center-to-center accuracy is the lateral centering of the x-ray source 12 with respect to the lateral centerline of the detector 22. In an exemplary embodiment, the lateral centerline of the detector 22 is defined by the center row of image matrix 60. Because the size of image matrix 60 is known and the number of rows and columns defining matrix 60 are known, the center row which corresponds to the lateral centerline of the image matrix also is known. Laterally centering source 12 with respect to the lateral centerline of detector 22 ensures that an x-ray field 16 generated by source 12 will impact and be detected by detector 22, thus decreasing the occurrence of image decentering or anatomical cutoff As can be appreciated by those of skill in the art, other techniques for designating the lateral centerline of detector 22 may also be used, such as a physical measurement of detector 22 and/or assignment of a constant representing a measured, or even an assumed, centerline.

Figure 3:
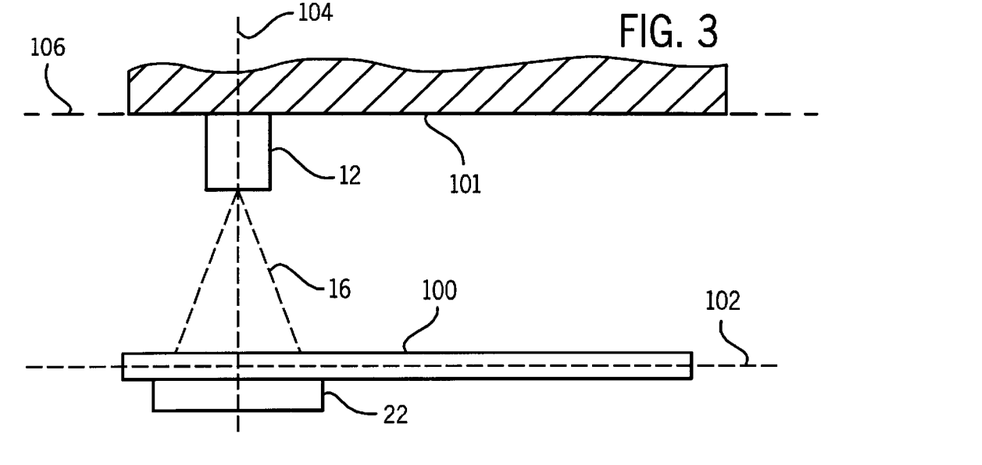
FIG. 3 is a side view of certain of the image acquisition components of the system of FIG. 1, and, in particular, illustrates the orientation of an x-ray source with respect to a digital x-ray detector associated with a patient positioner.
Figure 4:
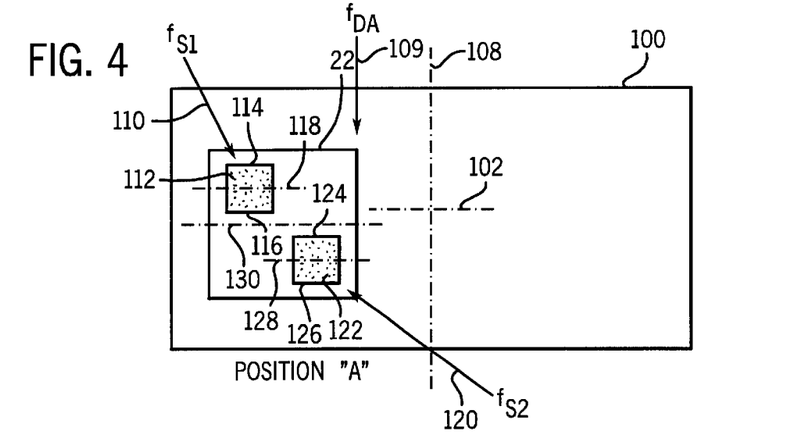
FIG. 4 is an elevational view of the exemplary patient positioner and detector of FIG. 3, illustrating the detector positioned at one end of the positioner, and the impact on the detector of x-ray fields generated by the x-ray source when positioned at various source locations.
Figure 5:
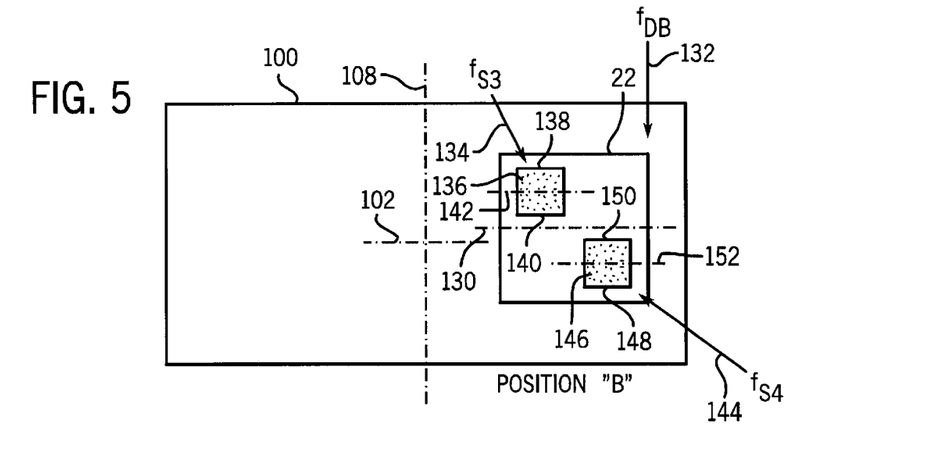
FIG. 5 is an elevational view of the positioner and detector of FIG. 3, illustrating the detector positioned at the other end of the positioner and the impact on the detector of x-ray fields generated while the x-ray source is at other various source locations.

An exemplary technique for determining laterally centered positions of the x-ray source 12 with respect to the detector 22 maybe understood with reference to FIGS. 3–5. Turning first to FIG. 3, x-ray source 12 is shown movably mounted to a support structure 101 and positioned with respect to detector 22, which is associated with a patient positioner 100. Although the positioner 100 is illustrated in a horizontal orientation, it should be understood that positioner 100 may be either a horizontal positioner, such as a patient table, or an upright positioner. Further, it should be understood that the terms longitudinal, lateral, and vertical, shall be used to provide a frame of reference only. For example, with reference to FIG. 3, the detector 22 is disposed along a translational axis 102, which is illustrated in a horizontal, or longitudinal, orientation. However, translational axis 102 may in fact have a vertical orientation if, for instance, the detector 22 were associated with an upright positioner 100.

As shown in FIG. 3, source 12 is vertically displaced from detector 22 along a vertical axis 104. The source 12 is further longitudinally positioned with respect to the detector 22 along a source translational axis 106. In an exemplary embodiment, the source translational axis 106 is substantially parallel to the detector translational axis 102. Further, the detector 22 is movable along the detector translational axis 102, such that detector 22 may be positioned at any location along the length of the positioner 100. The source 12 is movable along the source translational axis 106 such that the source 12 may longitudinally track the position of detector 22. The source 12 also is movable along the vertical axis 104, such that the source 12 may be moved to a position that is either closer or further removed from the detector 22. Still further, the source 12 is movable laterally with respect to the translational axis 106, such that the source 12 can be centered both longitudinally and laterally with respect to the detector 22. For reference, the lateral axis of movement 108 is illustrated in FIG. 4.

FIG. 4 is a plan view of the positioner 100 and its associated detector 22. FIG. 4 illustrates the first step in a setup procedure for determining a laterally centered position of the source 12 with respect to a lateral centerline 130 of the detector 22. As illustrated in FIG. 4, the detector 22 is located at a first position "A", referenced generally by the numeral 109, along the detector translational axis 102. In an exemplary implementation of the setup technique, the position A is disposed at one end of positioner 100, but the setup procedure contemplates that detector 22 could be positioned at any location along the detector longitudinal axis 102. The x-ray source 12 is then moved to a first location 110 at which it can generate an x-ray field that can be detected by the detector 22 at position A. In an exemplary embodiment, when the source is at location 110, an x-ray field impacts the area at one corner of the detector 22, as illustrated in FIG. 4. Further, in the exemplary embodiment illustrated, position sensor 19 provides an electrical feedback signal, $f_{DA}$, to system controller 28 which is representative of detector position 109, and position sensor 18 provides an electrical feedback signal, $f_{s1}$, to system controller 28 which is representative of the source position 110.

While the source is positioned at location 110, the source 12 is energized such that an x-ray field 112 impacts detector 22. Detector 22 detects x-ray field 112 and generates electrical signals representative thereof As described above, the detector controller 26 commands acquisition of the electrical signals generated in the detector 22 as a result of the x-ray field exposure. The acquired signals are processed by detector controller 26 and system controller 28 to determine the location of opposed, lateral peripheral edges 114 and 116 of the x-ray field 112. For example, the lateral edges 114 and 116 may be determined by scanning each row of the detector and comparing adjacent scanned rows until a substantial variation between the signals read from adjacent rows is detected. Such a substantial variation may be representative of a lateral peripheral edge of the x-ray field 112. However, it should be understood that the lateral edges can be detected in other manners, as would be appreciated by one of ordinary skill in the art. Once the rows corresponding to the lateral edges 114 and 116 are determined, the readout corresponding to lateral center row 118 of the field 112 may be determined:

$$row_1 = \frac{row_{12} + row_{11}}{2}$$

where "$row_1$" represents lateral center row 118 readout, "$row_{12}$" represents the row readout corresponding to the lateral edge 114 of the x-ray field 112, and "$row_{11}$" represents the row readout corresponding to the lateral edge 116 of the x-ray field 112.

The source 12 is then moved to a second location 120 which is displaced from the first location 110 at least in the lateral direction. However, it should be understood that the location 120 may be displaced from the location 110 in the longitudinal direction as well as the lateral direction. Source position sensor 18 provides an electrical feedback signal, $f_{s2}$, to system controller 28 which is representative of source location 120. While at location 120, the source 12 is energized to produce a second x-ray field 122 which is detectable by the detector 22 when at the position A. In the exemplary embodiment, illustrated in FIG. 4, the location 120 is disposed at a corner of detector 22 that is diagonally opposed to the corner of detector 22 at which the x-ray field 112 was detected. However, it should be understood that location 120 may be any location that is displaced laterally with respect to location 110 and at which an x-ray field generated by source 12 can be detected by the detector 22 while at the position A.

As described above with respect to location 110, detector 22 detects the x-ray field 122, generates electrical signals representative of the detected field, and the detector controller 26 and system controller 28 determine the rows of detector 22 which correspond to the lateral edges 124 and 126 of the field 122. Once the rows corresponding to the lateral edges 124 and 126 are found, the readout corresponding to lateral center row 128 of field 122 can be determined by the following equation:

$$row_2 = \frac{row_{22} + row_{21}}{2}$$

where "$row_2$" represents the lateral center row 128 readout, "$row_{22}$" represents the row readout corresponding to the lateral edge 124, and "$row_{21}$" represents the row readout corresponding to the lateral edge 126 of x-ray field 122.

After determining the lateral center rows 118 and 128, a lateral gain relationship between the position feedback signals and the row readouts can be established that applies at least when detector 22 is positioned at the position A. This lateral gain relationship is represented by the following equation:

$$G_A = \frac{f_{S2} - f_{S1}}{row_2 - row_1}$$

where $G_A$ represents the lateral gain constant, "$f_{s2}$" represents the electrical feedback signal from position sensor 18 when the source 12 is positioned at location 120, "$f_{s1}$" represents the electrical signal generated by the position sensor 118 when the source 12 is positioned at the location 110, "$row_2$" represents the readout corresponding to the center lateral row of x-ray field 122, and "$row_1$" represents the readout corresponding to lateral center row of the x-ray field 118.

Because the detector row readout corresponds to the edge detection of the x-ray fields, the difference, $row_2-row_1$, can be computed with the following equation:

$$row_2 - row_1 = \frac{row_{22} + row_{21} - row_{12} - row_{11}}{2}$$

Thus, the lateral gain constant can be represented by the following equation:

$$G_A = \frac{2(f_{S2} - f_{S1})}{row_{22} + row_{21} - row_{12} - row_{11}}$$

In alternative embodiments, the lateral gain constant, $G_A$, can be determined with increased accuracy by generating additional x-ray fields, determining the corresponding data points (i.e., center rows and corresponding feedback signals), and averaging the results.

The determination of the lateral gain relationship allows for the calculation of the laterally centered position of the source 12 with respect to the lateral centerline 130 of the detector 22 when the detector 22 is located at position A. This laterally centered source position may be expressed in terms of the electrical signal generated by source position sensor 18 as follows:

$$f_A = G_A row_C + (f_{S1} - G_A row_1)$$

where "$f_A$" represents the electrical signal from the position sensor 18 when the source 12 is centered laterally with respect to the detector 22, and "$row_c$" represents the detector row readout corresponding to the lateral centerline 130 of the detector 22.

Having determined the laterally centered position of source 12 in terms of electrical signal, $f_A$, from the feedback sensor 118, a subsequent user of imaging system 10 can be assured that the source 12 is substantially laterally centered with respect to the centerline of the detector 22 when the detector 22 is located at position 109 and the sensor 18 signal corresponds to $f_A$. In an exemplary embodiment, system 10 provides a visible or audible alarm (e.g., a flashing light, a display on the monitor of the user interface, a beeping sound, etc.) to indicate to the user that the source 12 is at the laterally centered position as indicated by the feedback signal, $f_A$, generated by the position sensor 118. Alternatively, or in addition to the alarm indication, the system controller 28 can be configured to generate a command signal which is applied to the motion control circuitry in control circuit 24 to apply a brake that substantially halts further movement of the source 12 upon receipt of a feedback signal, $f_A$, from position sensor 18 which corresponds to the determined laterally centered position.

In systems in which a linear relationship exists between the longitudinal position feedback signal generated by position sensor 18 and the longitudinal position feedback signal generated by detector position sensor 19, it can be assumed that the laterally centered source position with respect to the detector 22 when the detector 22 is at any position along the detector longitudinal axis 102 can be determined utilizing the lateral gain constant, $G_A$. Generally, such a linear relationship may be found in systems in which the translational track along which source 12 moves is substantially parallel with the translational track along which the detector 22 moves. However, in many systems, non-parallelism between the translational tracks may exist as a consequence of imperfect installation of the x-ray source suspension structure with respect to the attachment of the detector 22 to the positioner 100.

To compensate for any non-parallelism, the setup procedure can be repeated at a second detector position B, referenced generally by the numeral 132, as illustrated in FIG. 5. In the illustrated embodiment, position B is at the opposite end of the positioner 100. However, the setup procedure for determining the variable lateral centered source position can be performed at any position of the detector 22 along the detector translational axis 102 that is displaced from position A. As discussed above, position sensor 19 provides an electrical feedback signal, $f_{DB}$, to system controller 28 which is representative of detector position 132.

With detector 22 positioned at position 109, x-ray source 12 is then moved to a source location 134, at which it can generate an x-ray field that can be detected by the detector 22. In an exemplary embodiment, when the source is at location 134, an x-ray field impacts the area at one corner of the detector 22, as illustrated in FIG. 5. Position sensor 18 provides an electrical feedback signal to system controller 28 which is representative of the source position 134. While the source is positioned at location 134, the source 12 is energized such that an x-ray field 136 is generated that impacts detector 22. Detector 22 detects x-ray field 136 and generates electrical signals representative thereof. Detector controller 26 commands acquisition of the electrical signals generated in detector 22 as a result of the x-ray field exposure. The acquired signals are processed by detector controller 26 and system controller 28 to determine the location of the opposed lateral peripheral edges 138 and 140 of the x-ray field 136, as described above. Once the rows of the detector 22 image matrix that correspond to the opposed lateral edges 138 and 140 are determined, a lateral center row 142 of the field 136 may be determined, as described above.

The source 12 is then moved to a source location 144 which is displaced from the source location 134, at least in the lateral direction. However, it should be understood that location 144 may be displaced from location 134 in the longitudinal direction as well as the lateral direction. Source position sensor 18 provides an electrical feedback signal, $f_{S2}$, to system controller 28 which is representative of source location 144. While at location 144, source 12 is energized to produce an x-ray field 146 which is detectable by the detector 22 when at the detector position B. In the exemplary embodiment illustrated in FIG. 5, when the source is at the location 144, an x-ray field impacts the area at a corner of detector 22 that is diagonally opposed to the corner of detector 22 at which the x-ray field 136 was detected. However, it should be understood that location 144 may be any location that is displaced laterally with respect to location 134 and at which an x-ray field generated by source 12 can be detected by detector 22 while at the detector position B.

As described above, detector 22 detects the x-ray field 146, generates electrical signals representative of the detected field, and the detector controller 26 and system controller 28 determine the rows of the image matrix of the detector 22 which correspond to the opposed lateral edges 148 and 150 of the field 146. Once the rows corresponding to the lateral edges 148 and 150 are found, the lateral center row 152 of field 146 can be determined as set forth above.

After establishing the lateral center rows 142 and 152 readouts, a lateral gain relationship between the position feedback signals and the row readouts can be established that applies when detector 22 is positioned at the detector position B. This lateral gain relationship can be determined in the same manner as set forth above with respect to determining the lateral gain relationship when the detector 22 is positioned at the detector position B, and can be represented by the following equation:

$$f_B = G_B \text{row}_C + (f_{S3} - G_B \text{row}_3)$$

where "$f_B$" represents the electrical signal from the position sensor 18 when source 12 is centered laterally with respect to detector 22 when detector 22 is at position B, $G_B$ represents the lateral gain constant at detector position B, "row$_c$" represents the detector row readout corresponding to the known lateral centerline 130 of detector 22, "$f_{S3}$" represents the electrical feedback signal from position sensor 18 when the source 12 is positioned at location 134, and "row$_3$" represents the lateral center row 142 of x-ray field 136.

As discussed above, $G_B$ can be determined with increased accuracy by generating additional x-ray fields, determining the corresponding data points (i.e., center rows and corresponding feedback signals), and averaging the results.

The feedback signals from the position sensors, $f_A$ and $f_B$, can be utilized to define a longitudinal gain relationship along the translational, or longitudinal, axis 102 of detector 22. Assuming, in a general case, a linear relationship between the source position feedback signals and the detector position feedback signals, the longitudinal gain relationship can be expressed as:

$$G_y = \left( \frac{f_{SA} - f_{SB}}{f_{DA} - F_{DB}} \right)$$

where $G_y$ represents the longitudinal gain constant, $f_{SA}$ represents the feedback signal generated by sensor 18 when source 12 is centered laterally with respect to detector 22 at detector position A, $f_{SB}$ represents the feedback signal generated by position sensor 18 when source 12 is centered laterally with respect to the detector 22 at detector position B, $f_{DA}$ represents the feedback signal from position sensor 19 when detector 22 is at position A, and $f_{DB}$ represents the feedback signal generated by position sensor 19 when detector 22 is at position B.

The longitudinal gain constant can be used to derive a generalized equation for a laterally centered source set point as a function of the feedback signals from position sensors 18 and 19. This generalized equation is:

$$f_S = G_y f_D + (f_{SB} - G_y f_{DB})$$

where "$f_s$" is the feedback signal generated by the source position sensor 18, and "$f_D$" is the feedback signal from the detector position sensor 19. Thus, the source can be laterally centered with respect to the detector lateral centerline for any position of detector 22 along the detector translational axis 102 based upon the detector and source feedback position signals.

The setup procedure described above can be further generalized to account for the variance between the theoretical, or known, centerline of the detector 22 and the focal spot of source 12 as a function of the separation distance between source 12 and detector 22 along the vertical axis 104. That is, the setup procedure described above can be repeated with the source positioned with respect to detector 22 at various locations along the vertical axis 102. Thus, a variable laterally centered source setpoint can be determined for any position of the detector 22 along the longitudinal axis 102 in combination with any location of source 12 along the vertical axis 104 based on the determination of a source-to-detector separation gain constant.

Further, it should be understood that the determination of gain relationships and laterally centered setpoints described above has been determined by performing two x-ray exposures and calculating the corresponding data points at least two detector locations. It should be understood, however, that the described technique can provide more accurate results by performing additional x-ray exposures at the detector locations, calculating the corresponding data points, and averaging the results. Still further, additional exposures can be performed at additional detector locations and/or source locations, and the results can be averaged to enhance accuracy. Moreover, it is contemplated that gain constants and laterally centered setpoints can be determined using other appropriate equations rather than the specific equations set forth above. Such other equations may also have a form other than the linear forms described above, such as a polynomial form, which may contribute to enhanced accuracy of the computed results.

For the methodology described above, it has been understood that a field engineer is present at the location of system 10 to perform the setup procedure, including the determination of the variable laterally centered source setpoint. However, it is contemplated that the setup procedure can be performed from a location that is remote from the source 12 and detector 22. For example, the setup procedure can be initiated and controlled from a user interface or operator workstation that is coupled to system controller 28 via a network, such as the Internet. Further, it should be understood that the source 12 and/or the detector 22 can be positioned manually without the aid of motion control or motorized elements.

Further, the setup procedure has been described for a digital radiographic imaging system which includes a digital x-ray detector. It should be understood, however, that the setup procedure may be implemented in any digital imaging system having other types digital detectors, such as a detector based on charge coupled device technology. Further, the radiation source in the imaging system need not be an x-ray source, but can generate any type of radiation that is usefull in the imaging system and that can be detected by the system's detector.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for determining a variable lateral center-to-center setpoint for a digital imaging system having a digital detector and a radiation source, the method comprising:

providing the detector at a first detector position, the detector having a detector lateral centerline;

positioning the radiation source at a first source position along a source longitudinal axis;

generating a first radiation field with the radiation source, the first radiation field being detectable by the detector;

detecting the first radiation field at the detector;

determining a first lateral centerline of the first radiation field;

positioning the radiation source at a second source position, the second source position being laterally displaced from the first source position;

generating a second radiation field with the radiation source, the second radiation field being detectable by the detector;

detecting the second radiation field at the detector;

determining a second lateral centerline of the second radiation field; and determining a lateral gain constant based on the determined first and second lateral centerlines and the first and second source positions.

2. The method as recited in claim 1, further comprising: determining, based on the lateral gain constant, a centered lateral position of the source such that an x-ray field generated by the source is substantially centered with respect to the lateral centerline of the detector when the detector is at the first detector position.

3. The method as recited in claim 1, further comprising: providing a source position sensor;

sensing the first source position utilizing the source position sensor;

generating a first sensor signal representative of the first source position;

sensing the second source position utilizing the source position sensor; and generating a second sensor signal representative of the second source position.

4. The method as recited in claim 1, wherein determining the first and second lateral centerlines comprises detecting laterally opposed peripheral edges of the first and second radiation fields, respectively.

5. The method as recited in claim 1, wherein positioning the source at the first and second source positions comprises:

generating first and second control signals to automatically position the source; and moving the source in response to the first and second control signals, respectively.

6. The method as recited in claim 5, wherein generating the first and second control signals comprises providing first and second control commands from a remote location.

7. The method as recited in claim 2, further comprising: positioning the detector at a second detector position displaced from the first detector position along a detector translational axis;

positioning the source at a third source position;

generating a third radiation field with the source, the third radiation field being detectable by the detector at the second detector position;

detecting the third radiation field at the detector;

determining a third lateral centerline of the third radiation field;

positioning the source at a fourth source position laterally displaced from the third source position;

generating a fourth radiation field with the source, the fourth radiation field being detectable by the detector at the second detector position;

detecting the fourth radiation field at the detector;

determining a fourth lateral centerline of the fourth radiation field; and determining a second lateral gain constant based on the determined third and fourth lateral centerlines and the third and fourth source positions.

8. The method as recited in claim 7, further comprising automatically determining, based on the second lateral gain constant, a second centered lateral position of the source such that a radiation field generated by the source is substantially laterally centered with respect to the lateral centerline of the detector when the detector is at the second detector position.

9. The method as recited in claim 8, further comprising: utilizing the first and second lateral gain constants and the first and second detector positions to determine a translational gain constant; and utilizing the translational gain constant to determine a laterally centered source position at any detector position along the detector translational axis.

10. The method as recited in claim 9, further comprising: determining a source-to-detector gain constant; and utilizing the source-to-detector gain constant and the translational gain constant to determine a laterally centered source position at any source position along the source translational axis, at any detector position along the detector longitudinal axis, and at any source-to-detector separation distance.

11. The method as recited in claim 1, wherein the radiation source comprises an x-ray source.

12. A method for determining a lateral center-to-center setpoint of a digital imaging system having a radiation source that generates a radiation field detectable by a digital detector positioned at a first detector location, the method comprising:

determining a first lateral centerline of a first detected radiation field generated when the radiation source is at a first source position;

determining a second lateral centerline of a second detected radiation field generated when the radiation source is at a second source position laterally displaced from the first source position;

determining a first lateral gain constant based on the determined first and second lateral centerlines and the first and second source positions; and utilizing the first lateral gain constant to determine a laterally centered source position at which a radiation field generated by the source is substantially laterally centered with respect to a lateral centerline of the detector.

13. The method as recited in claim 12, wherein the digital detector comprises a plurality of rows and a plurality of columns that define an image matrix, and determining the first lateral centerline comprises determining first and second rows of the image matrix that correspond to opposed first and second peripheral lateral edges of the first detected radiation field.

14. The method as recited in claim 12, comprising:

wherein determining the first lateral gain constant and determining the laterally sensing positioning of the source with a source position sensor; and generating source position signals representative of each sensed source position, centered source position are further based on the source position signals.

15. The method as recited in claim 12, comprising:

positioning the digital detector to a second detector position location displaced from the first detector position along a detector translational axis;

determining a third lateral centerline of a third detected radiation field generated when the radiation source is at a third source position and the digital detector is at the second detector position, the third source position being displaced from the first source position at least along a source translational axis;

determining a fourth lateral centerline of a fourth detected radiation field generated when the radiation source is at a fourth source position and the digital detector is at the second detector position, the fourth source position being displaced from the third source position in a direction lateral to the source translational axis;

determining a second lateral gain constant based on the determined third and fourth lateral centerlines and the third and fourth source positions; and determining, based on the second lateral gain constant, a laterally centered source position at which a radiation field generated by the source is substantially laterally centered with respect to the lateral centerline of the detector when the detector is at the second detector position.

16. The method as recited in claim 15, comprising:

sensing positioning of the detector with a detector position sensor;

generating detector position signals representative of each sensed detector position;

determining a translational gain constant based on the first and second lateral gain constants and the detector position signals representative of the first and second detector positions; and determining, based on the translational gain constant, a laterally centered source position when the detector is at any position along the detector translational axis.

17. The method as recited in claim 12, comprising:

generating first and second control signals to automatically position the source at the first and second source positions, respectively; and moving the source in response to the first and second control signals.

18. The method as recited in claim 17, wherein generating the first and second control signals comprises providing first and second control commands from a location remote from the source and the detector.

19. The method as recited in claim 12, wherein the radiation source comprises an x-ray source.

20. A system for automatically determining a lateral center-to-center setpoint of a radiation source with respect to a digital detector, the system comprising:

a radiation source to generate a radiation field, the radiation source being movable at least along a source lateral axis and configured to generate a first radiation field at a first source position and a second x-ray field at a second source position, the second source position being laterally displaced from the first source position;

a digital detector to detect the first and second radiation fields and to generate detector signals representative of the first and second radiation fields, the detector having a lateral centerline; and a processing module configured to:
  determine a first lateral centerline of the first radiation field based on the detector signals representative of the first radiation field;
  determine a second lateral centerline of the second radiation field based on the detector signals representative of the second radiation field; and
  determine a lateral gain constant based on the first and second lateral centerlines and the first and second source positions.

21. The system as recited in claim 20, wherein the processing module is configured to:

utilize the lateral gain constant to determine a laterally centered source position at which a radiation field generated by the radiation source is laterally centered with the lateral centerline of the detector.

22. The system as recited in claim 20, comprising:

a source position sensor to provide sensor indicia representative of any source position.

23. The system as recited in claim 20, wherein the detector signals are representative of laterally opposed edges of each of the first and second radiation fields.

24. The system as recited in claim 20, wherein the radiation source is movable along a source translational axis transverse to the source lateral axis.

25. The system as recited in claim 24, wherein the detector is movable along a detector translational axis.

26. The system as recited in claim 25, wherein the source translational axis and the detector translational axis are substantially parallel.

27. The system as recited in claim 20, further comprising a user interface to provide a command to initiate determination of the lateral gain constant.

28. The system as recited in claim 27, wherein the command includes a command to position the source at the first and second source positions.

29. The system as recited in claim 27, wherein the user interface is at a location remote from the detector and the source.

30. The system as recited in claim 20, wherein the radiation source comprises an x-ray source.

* * * * *